United States Patent
Kahmer

(10) Patent No.: US 11,826,268 B2
(45) Date of Patent: Nov. 28, 2023

(54) TRIAL INSERTER AND TRIAL HEAD

(71) Applicant: GLOBUS MEDICAL, INC., Audubon, PA (US)

(72) Inventor: Damien Kahmer, Warrington, PA (US)

(73) Assignee: Globus Medical Inc., Audubon, PA (US)

( * ) Notice: Subject to any disclaimer, the term of this patent is extended or adjusted under 35 U.S.C. 154(b) by 0 days.

(21) Appl. No.: 17/806,967

(22) Filed: Jun. 15, 2022

(65) Prior Publication Data
US 2022/0304830 A1 Sep. 29, 2022

Related U.S. Application Data

(62) Division of application No. 16/213,164, filed on Dec. 7, 2018, now Pat. No. 11,369,491.

(51) Int. Cl.
| | |
|---|---|
| A61F 2/46 | (2006.01) |
| A61F 2/30 | (2006.01) |
| A61F 2/44 | (2006.01) |

(52) U.S. Cl.
CPC .......... *A61F 2/4684* (2013.01); *A61F 2/4611* (2013.01); *A61F 2/442* (2013.01); *A61F 2/4455* (2013.01); *A61F 2/4603* (2013.01); *A61F 2002/30082* (2013.01); *A61F 2002/4615* (2013.01)

(58) Field of Classification Search
CPC .... A61F 2/4684; A61F 2/4611; A61F 2/4603; A61F 2/44; A61F 2/46; A61F 2/442; A61F 2/4455; A61F 2/447; A61F 2002/4615; A61F 2002/30082

USPC .............................................. 623/17.11–17.16
See application file for complete search history.

(56) References Cited

U.S. PATENT DOCUMENTS

| | | | |
|---|---|---|---|
| 4,714,469 A | 12/1987 | Kenna | |
| 5,885,299 A * | 3/1999 | Winslow | A61B 17/861 606/247 |
| 6,174,311 B1 * | 1/2001 | Branch | A61B 17/1671 606/86 A |
| 6,712,819 B2 | 3/2004 | Zucherman et al. | |
| 7,510,567 B2 | 3/2009 | Zucherman et al. | |
| 7,811,292 B2 | 10/2010 | Lo et al. | |
| 7,918,891 B1 * | 4/2011 | Curran | A61F 2/442 623/17.16 |
| 8,216,316 B2 | 7/2012 | Kirschman | |
| 9,095,385 B2 | 8/2015 | Wallenstein et al. | |
| 11,369,491 B2 * | 6/2022 | Kahmer | A61F 2/4684 |
| 2012/0197317 A1 * | 8/2012 | Lezama | A61F 2/4611 606/86 A |
| 2017/0172759 A1 | 6/2017 | Kukkar et al. | |

\* cited by examiner

*Primary Examiner* — Marcela I. Shirsat

(57) ABSTRACT

Embodiments are directed to spinal treatments and, more particularly, to a trial inserter tool compatible with detachable trial heads for use in spinal surgery. In a preferred embodiment, the present invention provides a system for sizing an implant to be used in posterior lumbar interbody fusion surgery. The system may comprise a trial inserter tool, wherein the trial inserter tool comprises: a body, wherein the body is an elongated tubular, wherein the body comprises a first end and a second end; an actuation device, wherein the actuation device is disposed on the body between the first end and the second end; and a hooked support member that extends from the second end of the body; and a trial head disposable on the hooked support member.

15 Claims, 3 Drawing Sheets

TRIAL INSERTER AND TRIAL HEAD

CROSS-REFERENCE TO RELATED APPLICATIONS

The present application is a division of U.S. patent application Ser. No. 16/213,164, filed on Dec. 7, 2018, which is incorporated herein by reference.

BACKGROUND

Spinal fusion surgery may be a common procedure performed to relieve the pain and pressure on the spinal cord that may result from a number of different factors. Generally, spinal fusion may be performed to decompress and stabilize the spine. Spinal fusion generally may entail fusing adjacent vertebrae joints together. The most common drive to perform the surgery may be if a patient experiences degenerative disc disease to the point where the disc wears down and the joint between the vertebrae rubs. Generally, to fuse the adjacent vertebral bodies, the intervertebral disc may be first partially or fully removed. Bone graft may then be inserted between neighboring vertebrae to maintain normal disc spacing and restore spinal stability while facilitating an intervertebral fusion.

There are a number of known conventional fusion devices and methodologies in the art for accomplishing spinal fusion. These may include screw and rod arrangements, solid bone implants, and fusion devices which may include a cage or other implant mechanisms which, typically, may be packed with bone and/or bone growth inducing substances. These devices may be implanted between adjacent vertebral bodies in order to fuse the vertebral bodies together, alleviating the associated pain.

To properly size the implant mechanisms, trials may be used iteratively. For instance, traditional methods may include wherein an operator (typically a surgeon or other medical professional) inserts a trial in the disc space between adjacent vertebral bodies. The trial may model similar dimensions as the desired implant mechanism. The operator may insert a given number of trials into the disc space until the appropriate height and alignment has been reached. The size of that trial may embody the size of the implant mechanism to be used.

In the past, trials may have been fixed to an insertion tool. This may present unnecessary problems in preparation for, during, and/or after a surgery. For example, additional sterilization time may be required for each individual insertion tool that is fixed to a trial. Additionally, sorting through a large number of insertion tools to locate the desired trial may waste crucial time during a surgical procedure.

SUMMARY

In an exemplary embodiment, the present invention provides a system for sizing an implant. The system may include a trial inserter tool. The trial inserter tool may include a body, wherein the body is elongated, wherein the body includes a first end and a second end. The trial inserter may further include an actuation device, wherein the actuation device is disposed on the body between the first end and the second end. The system may further include a hooked support member that extends from the second end of the body. The system may further include a trial head releasably attachable to the hooked support member.

In another exemplary embodiment, the present invention provides a system for sizing an implant. The system may include a trial inserter tool. The trial inserter tool may include a body, wherein the body is an elongated tubular, wherein the body includes a first end and a second end, wherein a hole is disposed in the body between the first end and the second end. The trial inserter tool may further include a plunger disposed in the body, wherein the plunger is axially translatable in the body from a retracted position to an extended position with a distal end of the plunger extending from the second end of the body. The trial inserter tool may further include an actuation device coupled to the plunger and operable to move the plunger from the extended position to the retraced position, wherein the actuation device includes a sleeve and a button, wherein the sleeve is disposed around the body and positioned between the first end and the second end at the hole, wherein the sleeve is axially displaced in response to actuation of the button, wherein axial displacement of the sleeve is limited by the hole in the body is actuable to release an axis of motion for the sleeve. The system may further include a hooked support member that extends from the second end of the body, wherein the hooked support member includes an end extension that longitudinally extends from the second of the body and a main protrusion that protrudes from a distal end of the end extension towards a central axis of the trial inserter tool. The system may further include a trial head releasably attachable to the hooked support member. The trial head may include a head body. The trial head may further include a channel for receiving the end extension, wherein channel is formed in an outer surface of the head body and extends longitudinally from a first end of the head body. The trial head may further include a head hole for receiving the main protrusion and disposed in the channel at an end of the channel opposite the first end. The trial head may further include a recess disposed in the first end for receiving the plunger in the extended position to lock the trial head onto the trial inserter tool. The trial head may further include a marker disposed in the head body, wherein the marker is radioactive.

In another exemplary embodiment, the present invention provides a trial inserter tool. The trial inserter tool may include a body, wherein the body is elongated, wherein the body includes a first end and a second end. The trial inserter tool may further include an actuation device, wherein the actuation device is disposed on the body between the first end and the second end. The trial inserter tool may further include a plunger, wherein the plunger is disposed within the body. The trial inserter tool may further include a hooked support member, wherein the hook is disposed at the second end, wherein the hooked support member is operable to support a trial head on the trial inserter tool.

BRIEF DESCRIPTION OF THE DRAWINGS

These drawings illustrate certain aspects of some examples of the present invention, and should not be used to limit or define the invention, wherein.

DETAILED DESCRIPTION

Embodiments are directed to spinal treatments and, more particularly, to a trial inserter tool for use in spinal surgery that includes detachable trial heads. Embodiments of the trial inserter tool may include operation of a linear actuator to enable both attachment and detachment of a trial head. The trial inserter tool, combined with a trial head, may be inserted into a patient to size an implant to be disposed between a given set of vertebral bodies.

Embodiments of the trial inserter tool with detachable trial heads may be used in a wide variety of spinal treatments, including spinal fusion surgery. Without limitation, embodiments of use may be directed towards posterior lumbar interbody fusion (PLIF). In embodiments, PLIF surgery may be employed to eliminate pain experienced from degenerative disc disease and/or to correct spondylolisthesis. One aspect of PLIF surgery may be the sizing of an implant to be disposed in the intervertebral disc space that promotes the fusion of two adjacent vertebrae. Sizing may be done through the use of trial heads and a trial inserter tool.

A medical professional (e.g., a surgeon) may first prepare for the area to be treated. The medical professional may create an incision in the back of a patient and adjust the lower back muscles to access the desired area. Once the disc space is cleaned out of nucleus material, the medical professional may begin determining the proper size of an implant to be used by inserting a trial head with a trial inserter tool into the disc space. Typically, the trial head may model the exact dimensions of a specific implant. A plurality of trial heads may be inserted into the disc space before determining the correct size. As such, the plurality of trial heads may be detachable from the trial inserter tool, and a singular trial inserter tool may be used during the surgical procedure.

Figure 1A:
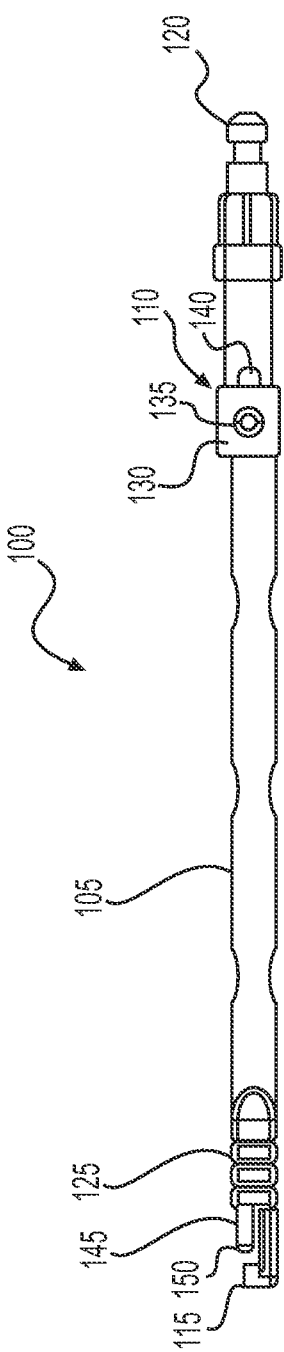
FIGS. 1A and 1B illustrate an embodiment of a trial inserter tool.
Figure 1B:
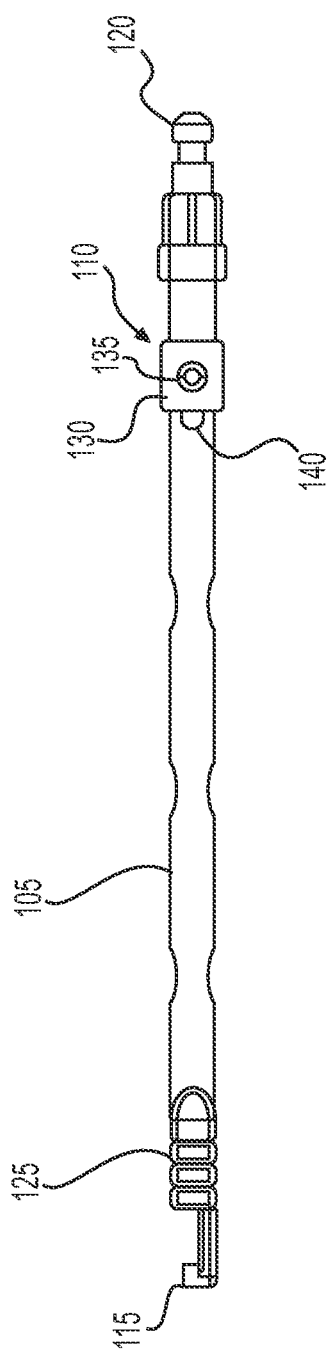

FIGS. 1A and 1B illustrate an embodiment of a trial inserter tool 100. FIG. 1A illustrates trial inserter tool 100 in an extended position for locking a trial head (e.g., trial head 300 on FIG. 3) onto trial inserter tool. FIG. 1B illustrates trial inserter tool 100 in a retracted position for releasing the trial head. Trial inserter tool 100 may be used to insert a trial head (discussed further below) into an intervertebral disc space between a given set of vertebral bodies during a surgical operation of a patient. In the illustrated embodiment, trial inserter tool 100 may include a body 105, an actuation device 110, and a hooked support member 115. The hooked support member 115 may support and position and trial head on the trial insert tool 100. The actuation device 110 may be operable to secure the trial head on the hooked support member 115. In operation, the body 105 may be elongated to deliver the trial head through an access channel and into the disc space.

In some embodiments, body 105 may include a first end 120 and a second end 125. In some embodiments, both first end 120 and second end 125 may close off the interior of body 105. Body 105 may be made of any suitable material. Without limitation, suitable materials may include metals, nonmetals, polymers, composites, ceramics, and/or combinations thereof. Body 105 may be any suitable size, height, and/or shape. Without limitation, a suitable shape may include, but is not limited to, cross-sectional shapes that are circular, elliptical, triangular, rectangular, square, hexagonal, and/or combinations thereof. In embodiments, body 105 may be a hollow, elongated tubular. In some embodiments, body 105 may have length in a range of from about 10 centimeters to about 100 centimeters. In some embodiments body 105 may have a width of about 5 centimeters to about 30 centimeters. However, the scope of the disclosure is not so limited to these dimensions for body 105. Rather, body 105 may have any suitable dimensions as desired for a particular application.

In some embodiments, trial inserter tool 100 may further include actuation device 110. Actuation device 110 may be secured onto body 105. In the illustrated embodiment, actuation device 110 may be disposed on body 105 between first end 120 and second end 125. Actuation device 110 may be operable to secure a trial head in place at second end 125. In some embodiments, actuation device 110 may include of a sleeve 130 and a button 135. Sleeve 130 may be made of any suitable material. Without limitation, suitable material may be metals, nonmetals, polymers, composites, ceramics, and/or combinations thereof. Sleeve 130 may be any suitable size, height, and/or shape. Without limitation, a suitable shape may include, but is not limited to, cross-sectional shapes that are circular, elliptical, triangular, rectangular, square, hexagonal, and/or combinations thereof. In embodiments, sleeve 130 may be a hollow tubular disposed around body 105. Sleeve 130 may have a shorter length than body 105. For example. Sleeve 13 may have a length of about 1 centimeters to about 15 centimeters.

In some embodiments, button 135 may be disposed on sleeve 130 at any suitable location. Button 135 may be any suitable size, height, and/or shape. In some embodiments, sleeve 130 may be displaced axially along body 105 by actuating button 135. For example, sleeve 130 may be secured onto body 105 at a fixed location. During operation, embodiments may include pressing or otherwise actuating button 135 in order to free an axis of motion for sleeve 130. As button 135 is actuated, sleeve 130 may be capable of displacing axially along body 105 a certain distance. In embodiments, the certain distance that sleeve 130 may be capable of traversing may be defined as the length of a hole 140 disposed through body 105. The distance that button 135 and sleeve 130 may travel may be limited by hole 140, as either button 135 and/or sleeve 130 may be coupled to a plunger 145 (e.g., shown on FIG. 1A) disposed inside trial inserter tool 100. For example, FIG. 1A illustrates trial inserter tool 100 in an extended position for securing a trial head onto hooked support member 115. When desired to release the trial head, for example, the button 135 may be depressed and sleeve 130 may then be axially displaced toward first end 120, as seen in FIG. 1B.

With specific reference to FIG. 1A, embodiments may include plunger 145 may disposed within body 105 of trial inserter tool 100. Plunger 145 may extend through body 105 to engage actuation device 110. As illustrated, a distal end 150 of plunger 145 may extend from second end 125 of body 105 in the extended position. Plunger 145 may be any suitable structure to be used as a linear actuator. Plunger 145 may be made of any suitable material and may be any suitable size, height, and/or shape. In embodiments, a medical professional may manually operate plunger 145 by actuating button 135 and displacing sleeve 130. In other embodiments, plunger 145 may be driven by hydraulics, pneumatics, electricity, and/or combinations thereof. In response to displacing sleeve 130, plunger 145 may travel axially through body 105 and partially out of body 105 at second end 125, as seen on FIG. 1A. The portion of plunger 145 that protrudes from second end 125 may be the same length as the length of hole 140. As best seen on FIG. 1B, plunger 145 may be fully retracted into body 105 in the retracted position.

Figure 2:
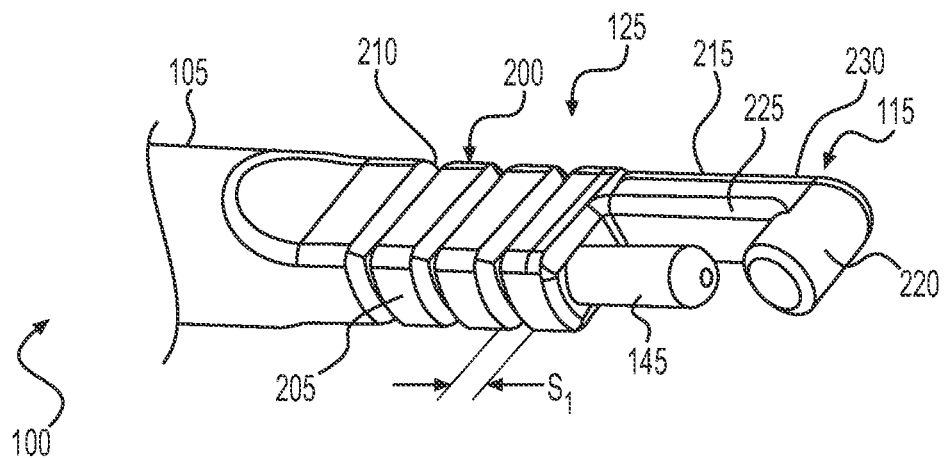
FIG. 2 illustrates an embodiment of a second end of a trial inserter tool.

FIG. 2 illustrates second end 125 of body 105 in more detail in accordance with example embodiments. As illustrated, plunger 145 may extend from second end 125, and second end 125 may also include a plurality of surface features 200. The plurality of surface features 200 may be used to accurately determine the length of a suitable implant to be used in a corresponding spinal surgery. In embodiments, the surface features 200 may be seen using fluoroscopy. Surface features 200 may include any suitable features on surface of second end 125 that may be visible through fluoroscopy of other suitable technique. For example, surface features 200 may include a plurality of spaced ridges 205. In the illustrated embodiment, there may be a plurality of grooves 210 disposed between adjacent ridges 205. In embodiments, the pluralities of ridges 205 may be have a pre-defined spacing. Without limitation, the pre-defined spacing of each ridge 205 may be from about 0.1 cm to about 5 cm.

As illustrated, hooked support member 115 may be disposed at second end 125 of body 105. In the illustrated embodiment, hooked support member 115 extends longitudinally from second end 125. Hooked support member 115 may serve to couple a trial head (e.g., trial head 300 shown on FIG. 3) to trial inserter tool 100 with the actuation of plunger 145. Hooked support member 115 may include an end extension 215 and a main protrusion 220. End extension 215 may be a further axial extension of material from body 105 at second end 125. End extension 215 and second end 125 may be unitary members or, in some embodiments, end extension 215 may be a separate piece coupled to second end 125. The inner side of end extension 215 may be chamfered and/or may include fillets. For example, end extension 215 may include chamfered inner surfaces 225. Main protrusion 220 may be a protrusion at a distal end 230 of end extension 215. As illustrated, main protrusion 220 may extend from end extension 215 toward central axis of trial inserter tool 100. In some embodiments, main protrusion 220 and end extension 215 may be perpendicular to each other. Main protrusion 220 may be any suitable size, height, and/or shape. Without limitation, a suitable shape may include, but is not limited to, cross-sectional shapes that are circular, elliptical, triangular, rectangular, square, hexagonal, and/or combinations thereof. In some embodiments, main protrusion 220 may be cylindrical. In some embodiments, the dimensions of hooked support member 115 and plunger 145 may align with those of a trial head, as discussed below.

Figure 3:
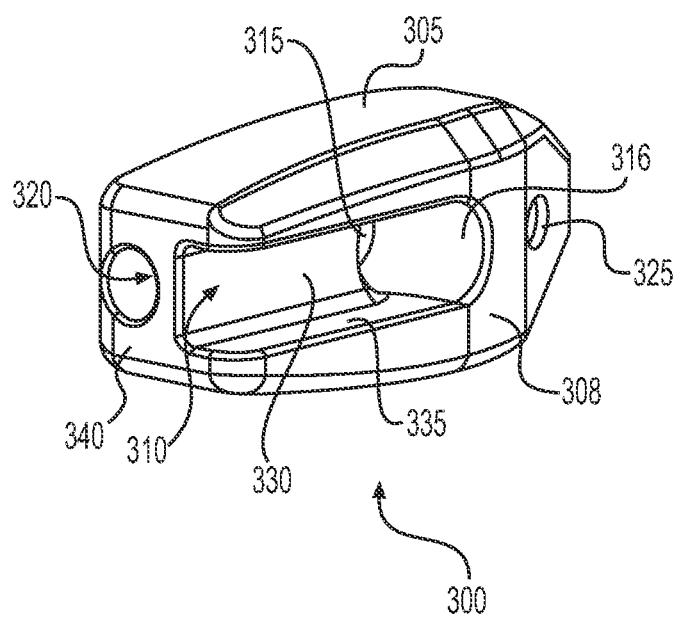
FIG. 3 illustrates an embodiment of a trial head.

FIG. 3 illustrates an embodiment of a trial head 300. Trial head 300 may be used to determine an appropriate width, height, length, and/or combinations thereof of a suitable implant to be disposed within a patient during a spinal surgery. Trial head 300 may be releasably attached to (e.g., referring to FIG. 1). In some embodiments, trial head 300 may be releasably attached to trial inserter tool 100 (e.g., referring to FIG. 1) to allow a medical professional to dispose trial head 300 into a disc space between a set of adjacent vertebral bodies. Trial head 300 may include a head body 305, a channel 310, a head hole 315, a recess 320, and a marker 325. Head body 305 may be made of any suitable material. Without limitation, suitable material may include metals, nonmetals, polymers, composites, ceramics, and/or combinations thereof. Head body 305 may be any suitable size, height, and/or shape. Without limitation, a suitable shape may include, but is not limited to, cross-sectional shapes that are circular, elliptical, triangular, rectangular, square, hexagonal, and/or combinations thereof. In embodiments, head body 305 may generally be an ovular shape.

As illustrated, trial head 300 may include an outer surface 308 in which channel may be disposed. Channel 310 may be a designated area of trial head 300 wherein material from head body 305 has been removed. As illustrated, channel 310 may extend along longitudinal axis of trial head 300. Channel 310 may include a base 330 and walls 335. In some embodiments, base 330 may be a part of head body 305 and may be a flat side of channel 310. In some embodiments, channel 310 may include two walls 335 that extend perpendicularly from base 330. As a result, channel 310 may generally be a rectangular space where head body 305 lacks material. In some embodiments, there may be fillets where walls 335 and base 330 join and/or walls 335 and base 330 may be chamfered. The length of channel 310 may traverse from a first end 340 of head body 305 to head hole 315.

Head hole 315 may be a hole disposed through head body 305 near in a central portion of head body 305. Head hole 315 may be disposed at an end 316 of channel 310 opposite from first end 340. Head hole 315 may be any suitable size and/or shape for receiving main protrusion 220 (e.g., referring to FIG. 2). Without limitation, a suitable shape may include, but is not limited to, cross-sectional shapes that are circular, elliptical, triangular, rectangular, square, hexagonal, and/or combinations thereof. In some embodiments, head hole 315 may have a circular cross-section. In certain embodiments, main protrusion 220 may be disposed through head hole 315. The diameter of head hole 315 may be greater than or equivalent to the diameter of main protrusion 220. When main protrusion 220 is disposed through head hole 315, plunger 145 (e.g., referring to FIG. 1A) may be actuated to displace into recess 320, thus securing trial head 100 to trial inserter tool 100.

Recess 320 may be an empty space within head body 305. Recess 320 may be disposed within the thickness of head body 305, and the length of recess 320 may run parallel to channel 310. In some embodiments, recess 320 may be formed at first end 340 of head body 305. Recess 320 may be any suitable size and/or shape for receiving plunger 145 (e.g., referring to FIG. 1A). Without limitation, a suitable shape may include, but is not limited to, cross-sectional shapes that are circular, elliptical, triangular, rectangular, square, hexagonal, and/or combinations thereof. In some embodiments, recess 320 may have a circular cross-section. In some embodiments, recess 320 may generally have the shape of a cylinder wherein one end is open and the other is closed. In certain embodiments, plunger 145 may be displaced into recess 320. The diameter of recess 320 may be greater than or equivalent to the shape of plunger 145.

With additional reference to FIGS. 1A, 1B, and 2, once trial head 300 is coupled to trial inserter tool 100 by disposing main protrusion 220 through head hole 315 and displacing plunger 145 into recess 320, trial inserter tool 100 may be used to insert trial head 300 into a patient. For example, trial inserter tool 100 may allow a medical professional to place trial head 300 through an access channel and into a disc space between a set of vertebral bodies in order to determine the size of a suitable implant that will be disposed between the vertebral bodies. In some embodiments, marker 325 may be disposed on trial head 300 in order to determine where trial head 300 is located once within the patient. Marker 325 may be disposed at any suitable location on trial head 300. While only a single marker 325 is shown, there may be a plurality of markers 325 disposed on trial head 300. In some embodiments, marker 325 may be radioactive, such that is may be seen using fluoroscopy. Marker 325 may be made of any suitable material and may be any suitable size, height, and/or shape. By visual verification of marker 325, a medical professional may be able to correctly position trial head 300 within a patient. As trial head 300 may be coupled to trial inserter tool 100 at second end 125, a medical professional may manipulate trial inserter tool 100 at first end 120 of trial inserter tool 100 to move trial head 300 in a corresponding direction. If necessary, trial head 300 may be removed from patient and a trial head 300 of a different size may be secured to trial inserter tool 100. The trial head 300 of a different size may then be inserted into the patient. This process may be repeated, for example, until the medical professional has determined an appropriate size for the implant.

Figure 4:
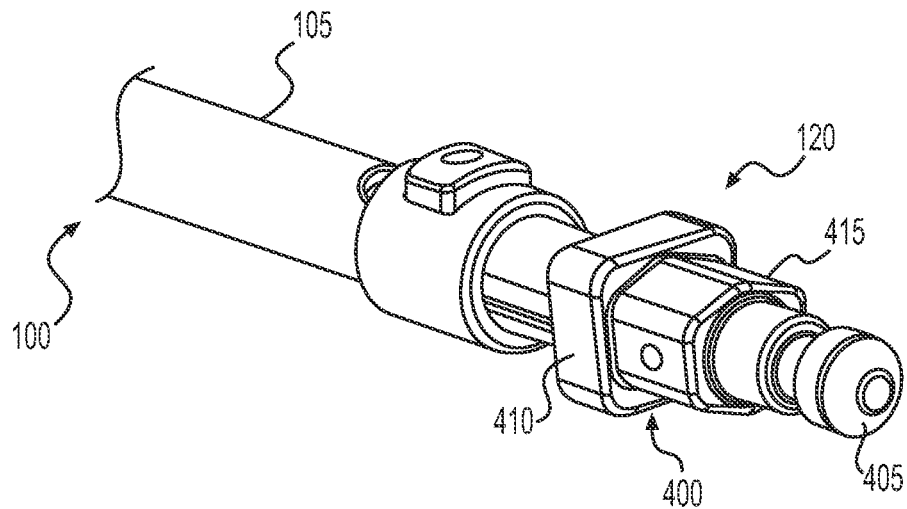
FIG. 4 illustrates an embodiment of a first end of a trial inserter tool.
Figure 5:
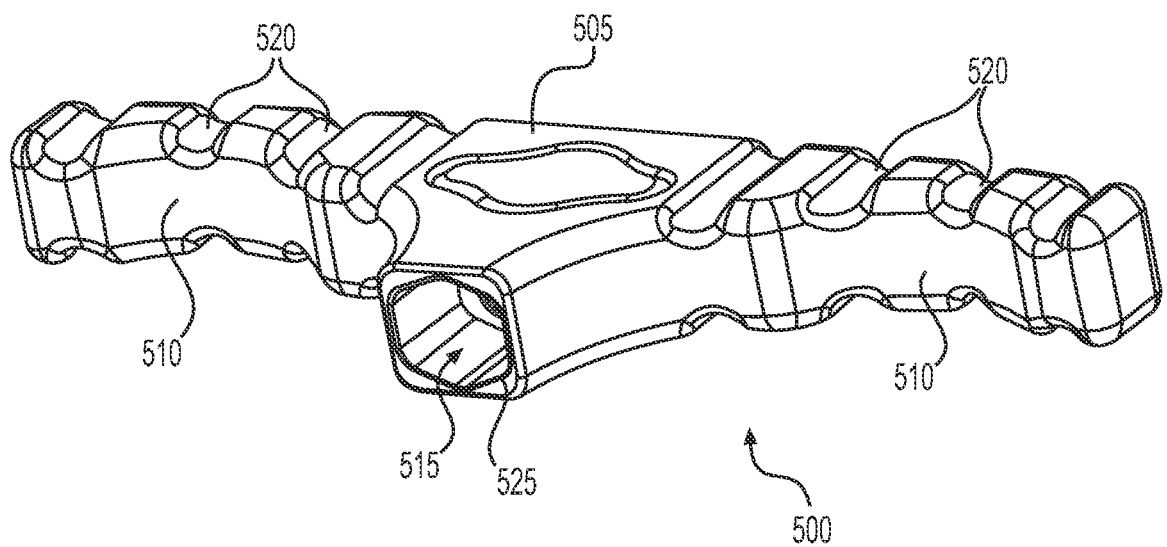
FIG. 5 illustrates an embodiment of a handle.

FIG. 4 illustrates an embodiment of first end 120 of body 105 of trial inserter tool 100. As illustrated, first end 120 may include an insertion feature 400 and a pin end 405. Insertion feature 400 may serve to be inserted into a handle (as illustrated in FIG. 5) that a medical professional may grip. Insertion feature 400 may be any suitable size, height, and/or shape. As illustrated, insertion feature 400 may include a base 410 and a protruding structure 415. In some embodiments, base 410 may be disposed adjacent to protruding structure 415. Without limitation, base 410 may have a square cross-sectional shape, and protruding structure 415 may have a hexagonal cross-sectional shape. As shown, pin end 405 may extend from an end of protruding structure 415 that opposes base 410.

In some embodiments, pin end 405 may serve as a fastening mechanism to couple first end 120 of body 105 to a handle. Pin end 405 may be any suitable size, height, and/or shape. In some embodiments, any other suitable technique used to fasten may be used. First end 120 may be secured to a handle through the use of suitable fasteners, threading, adhesives, welding, and/or combinations thereof. Without limitation, suitable fasteners may include nuts and bolts, washers, screws, pins, sockets, rods and studs, hinges and/or any combination thereof.

FIG. 5 illustrates an embodiment of a handle 500. Handle 500 may be gripped by a medical professional in order to operate trial inserter tool 100 (e.g., referring to FIG. 1). In the illustrated embodiment, handle 500 may include of a handle body 505, one or more arms 510, and a handle recess 515. Handle body 505 may be the main area of handle 500, for example, wherein the palm of a medical professional may be located when gripping handle 500. Handle body 505 may be made of any suitable material. Without limitation, suitable material may be metals, nonmetals, polymers, composites, ceramics, and/or combinations thereof. Handle body 505 may be any suitable size, height, and/or shape. Without limitation, a suitable shape may include, but is not limited to, cross-sectional shapes that are circular, elliptical, triangular, rectangular, square, hexagonal, and/or combinations thereof. In embodiments, handle body 505 may be T-shaped, wherein arms 510 extends outwards from handle body 505 to form the T-shape.

As illustrated, there may be two arms 510 extending outwards in different directions from handle body 505. Each arm 510 may include a plurality of arm grooves 520 disposed on each arm 510. In some embodiments, the plurality of arm grooves 520 may be shallow areas where material has been machined out of the arm 510 wherein the fingers of an operator may rest. In alternate embodiments, the plurality of arm grooves 520 may be deep areas wherein more material has been machined out of each arm 510. Without limitations, the plurality of arm grooves 520 may generally be semicircular.

In some embodiments, an operator may manually grip both handle 500 and trial inserter tool 100 (e.g., referring to FIG. 1) and couple them together. The operator may insert first end 120 (e.g., referring to FIG. 1) of trial inserter tool 100 into handle recess 515. Handle recess 515 may be an empty space within handle body 505. The length of handle recess 515 may run perpendicular to the lengths arms 510. In embodiments, handle recess 515 may be accessible by a handle opening 525 disposed in handle body 505. Handle recess 515 may be any suitable size and/or shape. Without limitation, a suitable shape may include, but is not limited to, cross-sectional shapes that are circular, elliptical, triangular, rectangular, square, hexagonal, and/or combinations thereof. In some embodiments, handle recess 515 may have a hexagonal cross-section. Further, an end opposite of handle opening 525 may be closed off. Handle recess 515 may generally have the shape of a hexagonal cylinder wherein one end is open and the other is closed. In certain embodiments, insertion feature 400 (e.g., referring to FIG. 4) and pin end 405 (e.g., referring to FIG. 4) may be displaced into handle recess 515 through handle opening 525. In those embodiments, the shape and size of handle recess 515 may be equivalent to the shape of protruding structure 415 (e.g., referring to FIG. 4). Protruding structure 415 may displace through handle recess 515 until base 410 (e.g., referring to FIG. 4) seats against handle 500. As base 410 seats against handle 500, pin end 405 may engage with handle recess 515 and lock handle 500 to trial inserter tool 100.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A trial inserter tool releasably attachable to a plurality of differently sized trial heads each having a longitudinal recess and a lateral recess laterally positioned relative to the longitudinal recess, comprising:
   an elongate body defining a central longitudinal axis;
   an actuator;
   a plunger longitudinally disposed in the body and adapted to be longitudinally translated by the actuator between a retracted position and an extended position so as to releasably insert the plunger into the longitudinal recess of the trial head, the plunger being radially offset from the central longitudinal axis;
   an extension radially offset from the central longitudinal axis and extending distally of the body, the extension and the plunger being disposed on opposite sides of the central longitudinal axis; and
   a lateral protrusion extending laterally from the extension and disposed distally of the plunger, and configured to be inserted into the lateral recess of the trial head, the lateral protrusion radially overlapping with the plunger.

2. The trial inserter tool of claim 1, wherein the actuator is coupled to the plunger such that the actuator and the plunger translate together, wherein translation of the actuation device and the plunger is limited by length of a hole disposed in the body, wherein the actuator includes a sleeve and a button, wherein the button is disposed on the sleeve, wherein the sleeve is disposed around the body of the trial inserter tool.

3. The trial inserter tool of claim 1, wherein a distal portion of the body includes a plurality of predefined spaced ridges that are visible under fluoroscopy.

4. The trial inserter tool of claim 3, wherein the ridges are spaced longitudinally and each ridge runs laterally to the elongate body.

5. The trial inserter tool of claim 1, further comprising an end extension that extends distally from the body and the lateral protrusion protrudes from a distal end of the end extension towards a central axis of the body.

6. The trial inserter tool of claim 1, further comprising a handle disposed on a proximal end of the body, wherein the proximal end includes an insertion feature and a pin end, wherein the insertion feature includes a base and a protruding structure, wherein the protruding structure is disposed into the handle, wherein the base abuts the handle, wherein the pin end engages with a recess within the handle to couple the handle to the body.

7. The trial inserter tool of claim 6, wherein the handle includes a handle body and two arms extending outwardly from the handle body.

8. A trial inserter tool, comprising:
- a body, wherein the body is elongated, wherein the body comprises a proximal end and a distal end;
- an actuator, wherein the actuator is disposed on the body between the proximal end and the distal end;
- a plunger, wherein the plunger is disposed within the body; and
- a hooked support member, wherein the hooked support member is disposed at the distal end, wherein the hooked support member is operable to support a trial head on the trial inserter tool, wherein the actuator is coupled to the plunger such that the actuator and the plunger translate together, wherein translation of the actuator and the plunger is limited by length of a hole disposed in the body, wherein the actuator comprises a sleeve and a button, wherein the button is disposed on the sleeve, wherein the sleeve is disposed around the body of the trial inserter tool.

9. The trial inserter tool of claim 8, wherein the plunger is operable to translate axially in the body in response to the actuator from a retracted position to an extended position in which a distal end of the plunger extends from the distal end of the body for receiving the trial head.

10. The trial inserter tool of claim 8, wherein the distal end comprises a plurality of spaced ridges.

11. The trial inserter tool of claim 8, wherein the hooked support member comprises an end extension that extends from the distal end of the body and a main protrusion that protrudes from a distal end of the end extension towards a central axis of the trial inserter tool.

12. The trial inserter tool of claim 8, further comprising a handle disposed on the proximal end of the trial inserter, wherein the proximal end comprises an insertion feature and a pin end, wherein the insertion feature comprises a base and a protruding structure, wherein the protruding structure is disposed into the handle, wherein the base abuts the handle, wherein the pin end engages with a recess within the handle to couple the handle to the trial inserter tool.

13. The trial inserter tool of claim 12, wherein the handle comprises a handle body and two arms extending outwards from the handle body.

14. A trial inserter tool releasably attachable to a plurality of differently sized trial heads each having a longitudinal recess and a lateral recess laterally positioned relative to the longitudinal recess, comprising:
- an elongate body;
- an actuator;
- a plunger longitudinally disposed in the body and adapted to be longitudinally translated by the actuator between a retracted position and an extended position so as to releasably insert the plunger into the longitudinal recess of the trial head; and
- a lateral protrusion disposed distally and laterally of the plunger, and configured to be inserted into the lateral recess of the trial head;
- wherein the actuator is coupled to the plunger such that the actuator and the plunger translate together, wherein translation of the actuation device and the plunger is limited by length of a hole disposed in the body, wherein the actuator includes a sleeve and a button, wherein the button is disposed on the sleeve, wherein the sleeve is disposed around the body of the trial inserter tool.

15. The trial inserter tool of claim 14, further comprising an extension extending distally of the body and the lateral protrusion extends laterally from the extension.

\* \* \* \* \*